(12) United States Patent
Kawaguchi et al.

(10) Patent No.: US 10,695,467 B2
(45) Date of Patent: Jun. 30, 2020

(54) ANTIBACTERIAL MEMBER

(71) Applicants: Kanazawa Medical University, Kahoku-gun, Ishikawa (JP); Kanazawa Institute of Technology, Nonoichi-shi, Ishikawa (JP); Onward Ceramic Coating Co., Ltd., Nomi-shi, Ishikawa (JP)

(72) Inventors: Masahito Kawaguchi, Ishikawa (JP); Norio Kawahara, Ishikawa (JP); Yoshitsugu Iinuma, Ishikawa (JP); Kazuhiro Shintani, Nonoichi (JP); Shinobu Oda, Nonoichi (JP); Makoto Taki, Nomi (JP)

(73) Assignees: Kanazawa Medical University, Kahoku-gun, Ishikawa (JP); Kanazawa Institute of Technology, Nonoichi-shi, Ishikawa (JP); Onward Ceramic Coating Co., Ltd., Nomi-shi, Ishikawa (JP)

( * ) Notice: Subject to any disclaimer, the term of this patent is extended or adjusted under 35 U.S.C. 154(b) by 0 days.

(21) Appl. No.: 16/348,607

(22) PCT Filed: Nov. 9, 2017

(86) PCT No.: PCT/JP2017/040366
§ 371 (c)(1),
(2) Date: May 9, 2019

(87) PCT Pub. No.: WO2018/088459
PCT Pub. Date: May 17, 2018

(65) Prior Publication Data
US 2020/0061248 A1    Feb. 27, 2020

(30) Foreign Application Priority Data

Nov. 11, 2016  (JP) .................. 2016-220236
Nov. 11, 2016  (JP) .................. 2016-220237

(51) Int. Cl.
*A61L 27/54* (2006.01)
*A61L 27/30* (2006.01)
*A61L 31/08* (2006.01)
*A61L 31/16* (2006.01)

(52) U.S. Cl.
CPC ............ *A61L 27/54* (2013.01); *A61L 27/303* (2013.01); *A61L 27/306* (2013.01); *A61L 31/084* (2013.01); *A61L 31/088* (2013.01); *A61L 31/16* (2013.01); *A61L 2300/106* (2013.01); *A61L 2300/404* (2013.01); *A61L 2430/02* (2013.01)

(58) Field of Classification Search
CPC ....... A61L 27/306; A61L 27/303; A61L 27/54
See application file for complete search history.

(56) References Cited

U.S. PATENT DOCUMENTS

| | | | |
|---|---|---|---|
| 2007/0202144 A1 | 8/2007 | Hellerbrand | |
| 2010/0203339 A1* | 8/2010 | Eryilmaz | ............. A61L 27/08 428/408 |
| 2012/0177936 A1 | 7/2012 | Suzuki | |

FOREIGN PATENT DOCUMENTS

| | | | |
|---|---|---|---|
| JP | 2000-205279 A | | 7/2000 |
| JP | 2007-527758 A | | 10/2007 |
| JP | 2010-189694 A | | 9/2010 |
| JP | 2012-100777 A | | 5/2012 |
| JP | 2016097018 A | * | 5/2016 |
| WO | 2010/122773 A1 | | 10/2012 |
| WO | 2011/021566 A1 | | 1/2013 |

OTHER PUBLICATIONS

Hasebe, T. et al. "Fluorinated diamond-like carbon as antithrombogenic coating for blood-containing devices", Wiley InterScience, Sep. 1, 2005, www.interscience.wiley.com, DOI: 10.101002/jbm.a.30512.*
International Search Report for corresponding App. No. PCT/JP2017/040366, dated Jan. 30, 2018.
Written Opinion for corresponding App. No. PCT/JP2017/040366, dated Jan. 30, 2018.
International Preliminary Report on Patentability for corresponding App. No. PCT/JP2017/040366, dated Oct. 3, 2018.

* cited by examiner

*Primary Examiner* — Gina C Justice
(74) *Attorney, Agent, or Firm* — Renner, Otto, Boisselle & Sklar, LLP

(57) ABSTRACT

An antibacterial member that maintains a high antibacterial property and a high osteoconductive property for a long duration is provided. The antibacterial member includes a DLC film (F-DLC film) 40 containing fluorine at least partially or entirely on an outermost surface of a base material 10. The F-DLC film has an element ratio (F/(F+C)) of 17% to 72% and a nanoindentation hardness of 2,000 MPa to 16,000 MPa. This maintains wear resistance and close contact, and obtains an antibacterial member that maintains a high antibacterial property and a high osteoconductive property for a long duration. The F-DLC film does not necessarily need to cover the entire outermost surface of the base material but may be disposed in a mottled pattern.

8 Claims, 16 Drawing Sheets

Figure 4

| SAMPLE | FLUORINE ELEMENT CONCENTRATION RATIO F/C+F (at.%) | BACTERIA | VIABLE BACTERIA NUMBER (CFU) | | ANTIBACTERIAL ACTIVITY VALUE |
|---|---|---|---|---|---|
| | | | 0H | 24H | |
| CONTROL (UNTREATED Ti ALLOY) | - | STAPHYLOCOCCUS AUREUS | $2.4 \times 10^4$ | $1.4 \times 10^6$ | - |
| | | E. coli | $2.5 \times 10^4$ | $4.0 \times 10^6$ | - |
| DLC | 0 | STAPHYLOCOCCUS AUREUS | $2.4 \times 10^4$ | $3.5 \times 10^4$ | 1.61 |
| | | E. coli | $2.5 \times 10^4$ | $4.5 \times 10^4$ | 1.95 |
| F-DLC | 4.1 | STAPHYLOCOCCUS AUREUS | $2.1 \times 10^4$ | $4.5 \times 10^5$ | 0.98 |
| | | E. coli | $3.2 \times 10^4$ | $8.9 \times 10^6$ | -0.25 |
| F-DLC | 5.4 | STAPHYLOCOCCUS AUREUS | $2.1 \times 10^4$ | $1.9 \times 10^5$ | 0.81 |
| | | E. coli | $3.2 \times 10^4$ | $8.3 \times 10^6$ | -0.21 |
| F-DLC | 17.46 | STAPHYLOCOCCUS AUREUS | $8.3 \times 10^4$ | <20 (NOT DETECTED) | 5.38 |
| | | E. coli | $2.7 \times 10^4$ | <20 (NOT DETECTED) | 5.33 |
| F-DLC | 24.09 | STAPHYLOCOCCUS AUREUS | $8.3 \times 10^4$ | <20 (NOT DETECTED) | 5.38 |
| | | E. coli | $2.4 \times 10^4$ | <20 (NOT DETECTED) | 5.28 |
| F-DLC | 30.2 | STAPHYLOCOCCUS AUREUS | $2.4 \times 10^4$ | <20 (NOT DETECTED) | 5.38 |
| | | E. coli | $2.5 \times 10^4$ | <20 (NOT DETECTED) | 5.31 |

Figure 5

| SPECIMEN | F ELEMENT CONCENTRATION RATIO F/C+F (at.%) | GAS FLOW RATIO C2H2/C3F8 AT F-DLC DEPOSITION | FILM THICKNESS (μm) | ROCKWELL INDENTATION TEST (HR) | NANO-INDENTATION HARDNESS (MPa) | FRICTION CO-EFFICIENT | WEAR AMOUNT (mg) | ELECTRIC RESISTANCE (Ω) |
|---|---|---|---|---|---|---|---|---|
| DLC(a-C:H) | 0 | 0 | 1.0 | 3 (PEELING) | 22,000 | 0.401 | 0.004 | 40 MΩ or higher |
| F-DLC(a-C:H,F) | 4.1 | 0.46 | 1.0 | 1 (ENTIRE PEELING) | 19,200 | 0.269 | 0.015 | 40 MΩ or higher |
| F-DLC(a-C:H,F) | 5.4 | 1 | 1.0 | 6 (NO PEELING) | 16,710 | 0.397 | 0.008 | 40 MΩ or higher |
| F-DLC(a-C:H,F) | 17.46 | 3 | 1.0 | 6 (NO PEELING) | 15,900 | 0.412 | 0.013 | 40 MΩ or higher |
| F-DLC(a-C:H,F) | 24.09 | 5 | 0.7 | 6 (NO PEELING) | 12,560 | 0.304 | 0.034 | 40 MΩ or higher |
| F-DLC(a-C:H,F) | 29.6 | 10 | 0.7 | 6 (NO PEELING) | 2,155 | 0.536 | 0.047 | 40 MΩ or higher |
| UHMWPE | 0 | - | - | - | 83 | 0.187 | 0.019 | 40 MΩ or higher |
| PTFE | 53.34 | - | - | - | 28 | 0.161 | 0.52 | 40 MΩ or higher |

| SAMPLE | V79 CELL COLONY NUMBER (CULTURE WITH 100% EXTRACTED SOLUTION) | COLONY FORMATION RAT (%) |
|---|---|---|
| V79 (NON-EXTRACTED CULTURE SOLUTION) | 45.6 | 100 |
| POLYETHYLENE (NON-TOXIC) | 49 | 107.5 |
| 0.1% ZDEC (TOXIC) | 0 | 0 |
| 0.25% ZDBC (TOXIC) | 0 | 0 |
| UNTREATED Ti ALLOY 100% EXTRACTED SOLUTION | 47 | 103.1 |
| DLC 100% EXTRACTED SOLUTION | 50.5 | 110.7 |
| F-DLC 100% EXTRACTED SOLUTION | 48.25 | 105.8 |

Figure 14

| | | PARAMETER | BV/TV<br>BONE VOLUME<br>(TISSUE VOLUME) | N.Mu.Oc/BS<br>MULTINUCLEAR OSTEOCLAST CELL<br>NUMBER (BONE SURFACE) | N.Ob/BS<br>OSTEOBLAST CELL<br>NUMBER (BONE SURFACE) | MAR<br>BONE CALCIFICATION<br>RATE | BFR/BV<br>BONE FORMATION RATE<br>(BONE VOLUME BASIS) | O.Th<br>OSTEOID WIDTH |
|---|---|---|---|---|---|---|---|---|
| | | UNIT | % | N/mm | N/mm | μm/day | %/year | μm |
| WITHOUT 04wF | AVERAGE | Avr. | 20.4561 | 0.8537 | 43.0996 | 17.2088 | 7899.3609 | 38.3108 |
| | DEVIATION | SD | 5.0924 | 0.3039 | 5.7750 | 4.9809 | 3390.4288 | 1.2154 |
| | ERROR | SE | 2.5462 | 0.1520 | 2.8875 | 2.4904 | 1695.2144 | 0.6077 |
| WITH 04wF | AVERAGE | Avr. | 21.5058 | 0.6495 | 44.6760 | 15.8426 | 6431.2852 | 39.1569 |
| | DEVIATION | SD | 14.1705 | 0.3426 | 11.1125 | 7.5268 | 3649.8656 | 5.7438 |
| | ERROR | SE | 7.0852 | 0.1713 | 5.5562 | 3.7634 | 1824.9328 | 2.8719 |
| vs WITHOUT 04wF | | T1 | 0.4481 | 0.2037 | 0.4062 | 0.3869 | 0.2886 | 0.3952 |
| | | P VALUE | NS | NS | NS | NS | NS | NS |
| WITHOUT 08wF | AVERAGE | Avr. | 35.3760 | 1.3858 | 25.6201 | 16.1151 | 4256.7690 | 30.0284 |
| | DEVIATION | SD | 8.7024 | 0.4789 | 8.5161 | 5.1523 | 2057.8809 | 7.4143 |
| | ERROR | SE | 4.3512 | 0.2395 | 4.2581 | 2.5762 | 1028.9405 | 3.7071 |
| WITH 08wF | AVERAGE | Avr. | 57.5397 | 0.9822 | 34.1514 | 18.1908 | 4745.5141 | 30.8915 |
| | DEVIATION | SD | 12.4179 | 0.2181 | 5.3417 | 1.2585 | 1403.2517 | 3.5157 |
| | ERROR | SE | 6.2089 | 0.1090 | 2.6709 | 0.6293 | 701.6258 | 1.7579 |
| vs WITHOUT 08wF | | T1 | 0.0151 | 0.0983 | 0.0749 | 0.2426 | 0.3550 | 0.4215 |
| | | P VALUE | 0.05 | NS | NS | NS | NS | NS |
| WITHOUT 12wF | AVERAGE | Avr. | 61.1714 | 1.7794 | 24.6586 | 14.4802 | 2818.1796 | 26.7092 |
| | DEVIATION | SD | 5.8841 | 0.3504 | 6.3501 | 3.1039 | 798.1095 | 3.3839 |
| | ERROR | SE | 2.9420 | 0.1752 | 3.1750 | 1.5520 | 399.0547 | 1.6919 |
| WITH 12wF | AVERAGE | Avr. | 72.7142 | 1.2785 | 27.7069 | 12.4997 | 2408.3403 | 21.1121 |
| | DEVIATION | SD | 5.1356 | 0.1932 | 7.3314 | 4.1199 | 1200.0637 | 5.2930 |
| | ERROR | SE | 2.5678 | 0.0966 | 3.6657 | 2.0599 | 600.0318 | 2.6465 |
| vs WITHOUT 12wF | | T1 | 0.0130 | 0.0289 | 0.2766 | 0.2369 | 0.2966 | 0.0669 |
| | | P VALUE | 0.05 | 0.05 | NS | NS | NS | NS |

| SAMPLE | BACTERIA | VIABLE BACTERIA NUMBER (CFU) | | ANTIBACTERIAL ACTIVITY VALUE |
| --- | --- | --- | --- | --- |
| | | 0H | 24H | |
| CONTROL (UNTREATED Ti ALLOY) | STAPHYLOCOCCUS AUREUS | $2.4 \times 10^4$ | $1.4 \times 10^6$ | - |
| | E. coli | $2.5 \times 10^4$ | $4.0 \times 10^6$ | - |
| F-DLC | STAPHYLOCOCCUS AUREUS | $2.4 \times 10^4$ | <20 (NOT DETECTED) | 5.38 |
| | E. coli | $2.5 \times 10^4$ | <20 (NOT DETECTED) | 5.31 |
| MOTTLED F-DLC | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |

Figure 19

| No. | BASE MATERIAL | TREATMENT | t (μm) | Ra (μm) | Rz (μm) | RSm (μm) | Rt (μm) | COMMENT |
|---|---|---|---|---|---|---|---|---|
| COMPARATIVE EXAMPLE 1 | TiAl6V4 | UNTREATED | - | 0.072 | 0.212 | 241.1 | 0.275 | - |
| COMPARATIVE EXAMPLE 2 | TiAl6V4 | F-DLC | 0.8 | 0.051 | 0.181 | 131.4 | 0.254 | WEAR RESISTANCE: GOOD |
| COMPARATIVE EXAMPLE 3 | TiAl6V4 | SEGMENT F-DLC | 0.8 | 0.121 | 0.656 | 445.23 | 0.882 | WEAR RESISTANCE: POOR |
| COMPARATIVE EXAMPLE 4 | TiAl6V4 | DLC+WPC+F-DLC | 0.8 | 0.291 | 2.429 | 37.248 | 3.078 | WEAR RESISTANCE: POOR |
| EXAMPLE 1 | TiAl6V4 | WEAK WPC+ F-DLC | 0.8 | 0.181 | 1.519 | 62.504 | 2.077 | WEAR RESISTANCE: EXCELLENT |
| EXAMPLE 2 | TiAl6V4 | STRONG WPC+ F-DLC | 0.8 | 0.321 | 2.436 | 61.611 | 3.205 | WEAR RESISTANCE: EXCELLENT |

Figure 20

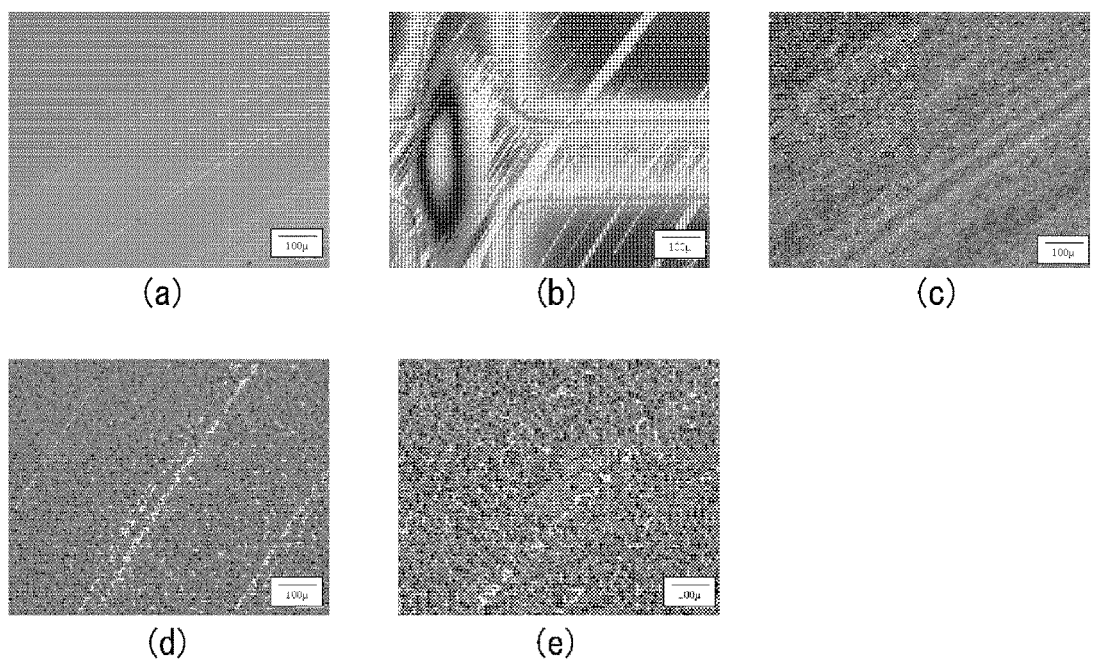

| SAMPLE | BACTERIA | VIABLE BACTERIA NUMBER (CFU) | | ANTIBACTERIAL ACTIVITY VALUE |
|---|---|---|---|---|
| | | 0H | 24H | |
| CONTROL (UNTREATED Ti ALLOY) | STAPHYLOCOCCUS AUREUS | $2.4 \times 10^4$ | $1.4 \times 10^6$ | - |
| | E. coli | $2.5 \times 10^4$ | $4.0 \times 10^6$ | - |
| F-DLC | STAPHYLOCOCCUS AUREUS | $2.4 \times 10^4$ | <20 (NOT DETECTED) | 5.38 |
| | E. coli | $2.5 \times 10^4$ | <20 (NOT DETECTED) | 5.31 |
| WEAK WPC+F-DLC | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |
| STRONG WPC+ F-DLC | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |
| F-DLC+ PSEUDO WORN STATE | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |
| WEAK WPC+F-DLC+ PSEUDO WORN STATE | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |
| STRONG WPC+F-DLC+ PSEUDO WORN STATE | STAPHYLOCOCCUS AUREUS | $3.8 \times 10^4$ | <20 (NOT DETECTED) | 5.00 |
| | E. coli | $1.9 \times 10^4$ | <20 (NOT DETECTED) | 5.20 |

ANTIBACTERIAL MEMBER

TECHNICAL FIELD

The present invention relates to an antibacterial member that can maintain a high antibacterial property and a high osteoconductive property for a long duration.

BACKGROUND ART

Implants such as an artificial joint and an internal fixation material have been widely used in the field of orthopedic surgery.

Resistance becomes extremely high when, for example, staphylococci and *E. coli* form a bio film on the surface of an implant, which makes it difficult to perform medical treatment. Thus, the implant needs to have an antibacterial property.

Examples of typically known surface treatment methods of providing the antibacterial property include a method of coating the implant surface with a metal layer made of, for example, silver or iodine, which is antibacterial, to dissolve out metal ions, a method of performing sustained-release of antibiotic substance, and a method of coating the implant surface with an antibacterial compound such as fluorine-based resins.

However, the methods of dissolving out metal ions and antibiotic substance have difficulties in maintaining the antibacterial property in a body for a long duration, and potentially cause toxicity and allergy. In addition, an antibacterial film wears due to friction between the implant surface and a bone or a surgical instrument during or after a surgery, which deteriorates the antibacterial property.

Screws and spinal cages as implant materials in the field of orthopedic surgery are expected to fuse with bones immediately after a surgery so that the duration of medical treatment is reduced and loosening of the screws, shift of the cages, and the like are prevented. Thus, coating provided on the surface of a screw or the like needs to have a high osteoconductive property.

A film containing diamond like carbon (hereinafter referred to as "DLC") has excellent wear resistance, friction resistance, chemical resistance, and corrosion resistance and high hardness, and thus is widely used as a protective film for a tool, a mold, a machine component, or the like. It is known that an F-DLC film obtained by adding fluorine to DLC has antithrombogenic and antibacterial properties for human body tissues such as muscle, blood, and blood vessels due to the characteristic of fluorine and has excellent biocompatibility.

In addition, it is already known that hydrogen-containing DLC, which contains no fluorine has a high osteoconductive property.

For example, Patent Literatures 1 and 2 disclose technologies of forming an intermediate layer such as a DLC film containing no fluorine on the surface of an implant, and forming an F-DLC film on the intermediate layer.

Patent Literature 3 discloses a technology of forming an F-DLC film on an implant having a surface roughness in a certain range.

In this manner, when the intermediate layer is provided or the implant surface is roughed to achieve an anchor effect, the sticking force of the F-DLC film onto the implant surface increases, which leads to reduction of occurrence of peeling to some extent.

CITATION LIST

Patent Literature

Patent Literature 1: Japanese Patent No. 5138127
Patent Literature 2: Japanese Patent No. 5661632
Patent Literature 3: Japanese Patent No. 4066440

SUMMARY OF INVENTION

Technical Problem

However, the above-described conventional technologies have problems as described below.

Specifically, it is thought that, as the addition rate of fluorine increases, the hardness of an F-DLC film significantly decreases and sufficient wear resistance and the like cannot be obtained. However, the wear resistance in a living body has not been necessarily clearly evaluated.

When the F-DLC film is disposed on an outermost surface as in the above-described conventional technologies, a decrease in the F-DLC film (layer thinning) is unavoidable due to wearing after an operation to insert the implant into a bone or after elapse of a certain duration on a slide surface of an artificial joint. As a result, the intermediate layer or a base material disposed below the F-DLC film is partially or entirely exposed, which potentially decreases the antibacterial property.

When an implant coated with the F-DLC film is used at a site such as the spine or the femur on which large external force acts, close contact between the F-DLC film and the intermediate layer is likely to decrease to cause peeling because of high stress generated at the interface between the implant and the film due to the hardness difference therebetween.

In particular, when an implant, on the entire surface of which the F-DLC film is formed, is bend as necessary for, for example, a spine rod or a fracture treatment plate, the F-DLC film is likely to peel off at the site of the bending.

These problems are common not only to implants used in the body but also to a general antibacterial member, for which the antibacterial property is required, such as a member used out of the body like an external fixator used for an open fracture or a member used being partially exposed out of the body.

The present invention is intended to solve the above-described problems and provide an antibacterial member that maintains a high antibacterial property and a high osteoconductive property for a long duration.

Solution to Problem

An antibacterial member according to the present invention includes a DLC film (F-DLC film) containing fluorine at least partially or entirely on an outermost surface of a base material. The F-DLC film has an element ratio (F/(F+C)) of 17% to 72% and a nanoindentation hardness of 2,000 MPa to 16,000 MPa.

The F-DLC film is disposed in a mottled pattern.

At least a DLC film containing no fluorine and the F-DLC film are sequentially coated on the surface of the base material, the surface of the base material is an irregular surface, and $Rz > t$ holds, where $t$ represents a thickness between the surface of the base material and a surface of the F-DLC film at deposition and $Rz$ represents a maximum height of section for a surface roughness of the F-DLC film at deposition.

A hydrogenated silicon carbide film is formed as a first layer directly above the base material, then a DLC film containing no fluorine is formed as a second layer, and then the F-DLC film is formed as a third layer.

A non-hydrogen DLC film is formed as a first layer directly above the base material, then a hydrogen-containing DLC film containing no fluorine is formed as a second layer, and then the F-DLC film is formed as a third layer.

The antibacterial member is a medical instrument inserted into or fixed to a bone.

Advantageous Effects of Invention

The inventors of the present application have found that it is possible to maintain wear resistance and close contact and maintain a high antibacterial property and a high osteoconductive property for a long duration when the F-DLC film as the outermost surface of the antibacterial member has an element ratio (F/(F+C)) of 17% to 72% and a nanoindentation hardness of 2,000 MPa to 16,000 MPa.

The F-DLC film does not necessarily need to cover the entire outermost surface of the base material, but may be disposed in a mottled pattern. In this case, too, an antibacterial effect by the F-DLC film is maintained. When the antibacterial member is bent, failure such as peeling due to crack generation can be reduced in a case in which the F-DLC film is formed in a mottled pattern as compared to a case in which the F-DLC film is formed on the entire outermost surface.

Excellent sticking force can be obtained when the non-hydrogen DLC film is formed as the first layer directly above the base material, then the hydrogen-containing DLC film containing no fluorine is formed as the second layer, and then the F-DLC film is formed as the third layer, or when the hydrogenated silicon carbide film is formed as the first layer directly above the base material, then the DLC film containing no fluorine is formed as the second layer, and then the F-DLC film is formed as the third layer.

The inventors of the present application have also found that it is possible to maintain wear resistance and close contact and maintain a high antibacterial property for a long duration when the surface of the base material is an irregular surface and Rz>t holds.

The antibacterial member according to the present invention is preferable as various body indwelling instruments (instrumentation) for surgeries of bone and inter-bone support, fixation, replacement, and bone insertion, which are used in the entire field of orthopedic surgery, and what is called medical instrument for dental implant, for example. Specifically, the antibacterial member is applicable to, for example, a spine fixation rod, a screw, pedicle screw and plate, a connector, a spine intervertebral fixation spacer, a cage, a transverse fixator, artificial joint stem, neck, and cup, an implant skull, a skull fixation plate, and a plate, a screw, a nail in a fracture surgery, and a dental implant.

However, the antibacterial member according to the present invention is not limited to these applications, but is also applicable to food instruments such as a food chopping blade and a food milling roller, and places that need to be antibacterial in home electronics such as a washing machine tub and an air conditioner.

BRIEF DESCRIPTION OF DRAWINGS

FIG. 4 illustrates a table listing, for example, the antibacterial activity value of each film.

FIG. 5 illustrates a table listing a result of evaluation of a physical property such as a nanoindentation hardness of each film.

FIG. 11 illustrates a table illustrates the number of V79 cell colonies and the colony formation rate of each culture solution.

FIG. 14 illustrates experiment data related to influence on bone formation in vivo.

FIG. 19 illustrates a table listing a result of measurement of the surface roughness of each film.

FIG. 20 illustrates an optical microscope image of wear indentation of each film after a friction and wear test: an image of a film of Comparative Example 2 in (a), an image of a film of Comparative Example 3 in (b), an image of a film of Comparative Example 4 in (c), an image of a film of Example 1 in (d), and an image of a film of Example 2 in (e).

FIG. 21 illustrates a table listing the antibacterial activity value and the like of each film after culture for 24 hours.

DESCRIPTION OF EMBODIMENT

The following describes an embodiment of an antibacterial member according to the present invention.

Figure 1:
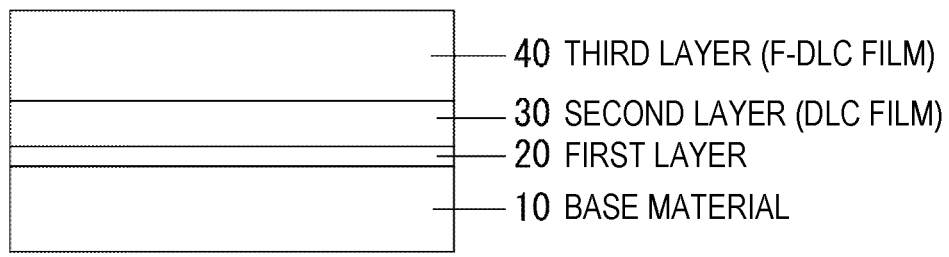
FIG. 1 is a cross-sectional view schematically illustrating a state in which first to third layers are formed on a base material.

As illustrated in FIG. 1, in the antibacterial member, at least a DLC film (second layer) 30 containing no fluorine and an F-DLC film (third layer) 40 containing fluorine are sequentially coated on the surface of a base material 10. In addition, in the present embodiment, a carbon compound layer (first layer) 20 is provided between the base material 10 and the DLC film 30.

The base material 10 may be a well-known metallic material. The shape of the base material 10 is not particularly limited but may be, for example, a plate shape, a bar shape, a linear shape, a helical shape, or a coil shape.

The carbon compound layer 20 is a layer formed on the surface of the base material 10 and functions as an underlayer when the DLC film 30 is formed on the surface of the base material 10. The material of the carbon compound layer 20 is not particularly limited but may be a publicly known material such as tetramethylsilane (TMS) typically used as an underlayer.

The DLC film 30 is a layer formed on the surface of the base material 10 (in the present embodiment, the surface of the carbon compound layer 20) and is a DLC film containing no fluorine.

The F-DLC film 40 is a layer formed on the surface of the DLC film 30 and is a DLC film containing fluorine. The F-DLC film 40 has an element ratio (F/(F+C)) of 17% to 72% and has a nanoindentation hardness of 2,000 MPa to 16,000 MPa.

The method of forming the carbon compound layer 20, the DLC film 30, and the F-DLC film 40 is not particularly limited but may be a well-known method such as a chemical evaporation coating method (CVD) or a physical evaporation coating method (PVD). Examples of the chemical evaporation coating method include a thermal CVD method and a plasma CVD method (including a high-frequency plasma CVD method). Examples of the physical evaporation coating method (PVD) include a sputtering method such as a high-output pulse sputtering method, an ion plating method such as an arc ion plating method, an ion beam evaporation coating method, and a plasma ion implantation method.

Example 1

[Deposition Method]

In the present example, a DLC film and an F-DLC film were formed by the high-frequency plasma CVD method (P-CVD method).

Specifically, the P-CVD method of an ICP scheme in which high-frequency power (13.54 MHz) is applied to a loop antenna was used. First, the outermost surface was etched by Ar ions. Then, a hydrogenated silicon carbide (SiC:H) film was deposited as the first layer by using tetramethylsilane (TMS) as a raw material. Then, a DLC film containing no additive such as fluorine was formed as the second layer by using acetylene ($C_2H_2$). Thereafter, an F-DLC film was formed as the third layer by using gas as mixture of propane octafluoride ($C_3F_8$) and acetylene at a predetermined ratio.

Normally, when $C_3F_8$ is used, the concentration of fluorine is low as compared to $CF_4$ and $C_2F_6$, which are typically used (because the concentration of fluorine depends on the element ratio of the gas). Thus, deposition conditions were optimized as follows to achieve a sufficient fluorine concentration.

First, vacuum discharge was performed to $1.0 \times 10^{-3}$ Pa, and then power of 100 W was supplied to the loop antenna, and a bias voltage of −2.5 kV was applied to a treatment target object (workpiece). In this state, Ar gas was introduced and the pressure was maintained at 0.3 Pa. Accordingly, the Ar gas was turned into plasma, and an oxide layer and the like on the surface of the workpiece were removed by Ar ions.

Subsequently, the introduction gas was changed from Ar to TMS and the pressure was maintained at 0.3 Pa so that a SiC:H film was formed as the first layer having a thickness of 0.1 μm approximately.

Subsequently, TMS was changed to acetylene and the pressure was maintained at 0.4 Pa so that a DLC film was formed as the second layer having a thickness of 0.1 approximately in the same manner.

Subsequently, acetylene and $C_3F_8$ were introduced at a gas flow ratio of 1:10 and the pressure was maintained extremely high at 3.7 Pa so that the third layer (F-DLC layer) having a thickness of 0.5 to 0.8 μm approximately was formed.

The element ratio of fluorine in the film of the F-DLC layer can be changed by changing the ratio of acetylene and $C_3F_8$. The first layer and the second layer are common to all Examples.

Pulsing the bias voltage enables treatment of an insulation target.

Although it is known that $C_3F_8$ can be used as F-DLC material gas, $CF_4$ and $C_2F_6$, which have higher fluorine content rates, are typically used. In the present invention, since the F-DLC film is formed by using $C_3F_8$, which has a larger molecular weight, it is possible to obtain a film having a sufficient fluorine content and thus a high antibacterial property while maintaining wear resistance.

However, when $C_3F_8$ is used as the material, it is impossible to provide coating with a film having a fluorine concentration equal to or higher than the gas element ratio (F/(F+C))=72.7%.

The use of fluorine-based gas, which has a further larger molecular weight, is also effective but is not necessarily preferable because the large molecular weight leads to excessive decrease of the addition rate of fluorine and a cost problem.

In the present Example, a film made of TMS is formed as the first layer on the surface of the base material and a DLC film is formed as the second layer. However, an F-DLC film may be directly formed on the surface of the base material without forming the first and second layers. Alternatively, the first and second layers may be formed of materials different from each other. When the different materials are used, for example, a DLC film having an excellent sticking force and containing no hydrogen in effect is formed as the first layer by an arc discharging method or a sputtering method, a hydrogen-containing DLC is formed as the second layer, and an F-DLC film is formed as the third layer. Simultaneously with arc discharging or sputtering discharging, a layer with slightly added hydrogen, hydrocarbon gas, or silane gas such as TMS may be inserted between the first layer containing no hydrogen and the second layer containing hydrogen. In such a case, it is further preferable to continuously change hardness by gradually changing a parameter such as a gas amount. The formation of the DLC film containing no hydrogen as the first layer more preferably uses a method such as a filtered arc method using a magnetic filter that reduces contamination with a foreign object called droplet and generated along with arc discharging into the film or a method that is unlikely to generate the droplet because the methods provide smooth and excellent close contact. In addition, the first and second layers preferably each have a film thickness of 50 nm to 500 nm approximately. This is because a film thickness with which a film having a physical strength is reliably formed is equal to or larger than 50 nm, and the film thickness needs to be 500 nm or smaller otherwise the first and second layers as films having high hardness would suffer film peeling due to high internal compressional stress of the films when the film thicknesses are large. In addition, the third layer (F-DLC layer) having a thickness of 0.5 to 0.8 approximately is formed to obtain excellent film sticking force. The third layer may be formed by the P-CVD method or a method of introducing gas such as C3F8 and performing deposition in the arc method or the sputtering method.

Alternatively, a Cr metal film is formed as the first layer, tungsten carbide (WC) or a coated structure of WC and an amorphous carbon film is formed as the second layer, and F-DLC is formed on the second layer.

[Element Ratio (F/(F+C))]

The element ratio of the F-DLC film was evaluated through element analysis by energy dispersive X-ray analysis (EDS) included in an electron microscope (SEM: JSM-6010LA manufactured by JEOL). The evaluation was performed under measurement conditions of an acceleration voltage of 5 kV and a magnification of 1,000. The evaluation was performed with the low acceleration voltage to accurately evaluate carbon and fluorine as much as possible, but the acceleration voltage may be increased to 15 kV approximately when another metal element is analyzed.

The EDS cannot analyze hydrogen in the film. Measurement of the element ratio of hydrogen is difficult, and neutron diffraction using radiation and a Rutherford backscattering analysis device need to be used. Thus, simple and fast evaluation is difficult and unrealistic, and evaluation results have large variation between measurement methods. For these reasons, each film was evaluated with the element ratio of F/(C+F) for sake of simplicity.

The evaluation of the element ratio of fluorine in the F-DLC film may include hydrogen (F/(C+F+H)). Actual evaluation found that a preferable film range was 14 to 72% for F/(H+C+F).

No large change occurs in the film characteristic in effect when small amounts of silicon, nitrogen, and the like are added into the film, and thus the film may contain other elements.

[Antibacterial Property]

Experiment data related to antibacterial performance of the antibacterial member according to the present invention is presented.

The antibacterial property of the surface of the F-DLC film was evaluated with different fluorine concentrations according to ISO 22196 as an international standard related to an antibacterial property test of a product provided with antibacterial processing.

Test solution using *Staphylococcus aureus* (ATCC29214) and *E. coli* (ATCC25922) was used. Samples were circular disks made of TiAl6V4 and having a diameter φ of 25 mm and a thickness of 3 mm. The samples include eight untreated samples (controlled samples) and eight samples having surfaces covered with F-DLC at the different fluorine concentrations. The test bacterial solution was dropped on each sample, and the sample was covered with a film and cultured in a petri dish at 35° C. for 24 hours. The test solution after the culture was washed out of the film and a test piece, and then the number of viable cells per unit area was determined for each specimen by counting the number of bacterial cells in the solution by an agar flat plate culture method.

An antibacterial activity value was calculated according to a formula below:

Antibacterial activity value=log(the number of viable cells in an unprocessed specimen)−log(the number of viable cells in an antibacterial processed specimen)

Typically, it is determined that an antibacterially-processed test piece has an antibacterial effect when the antibacterial activity value is equal to or larger than 2.0.

Figure 2:
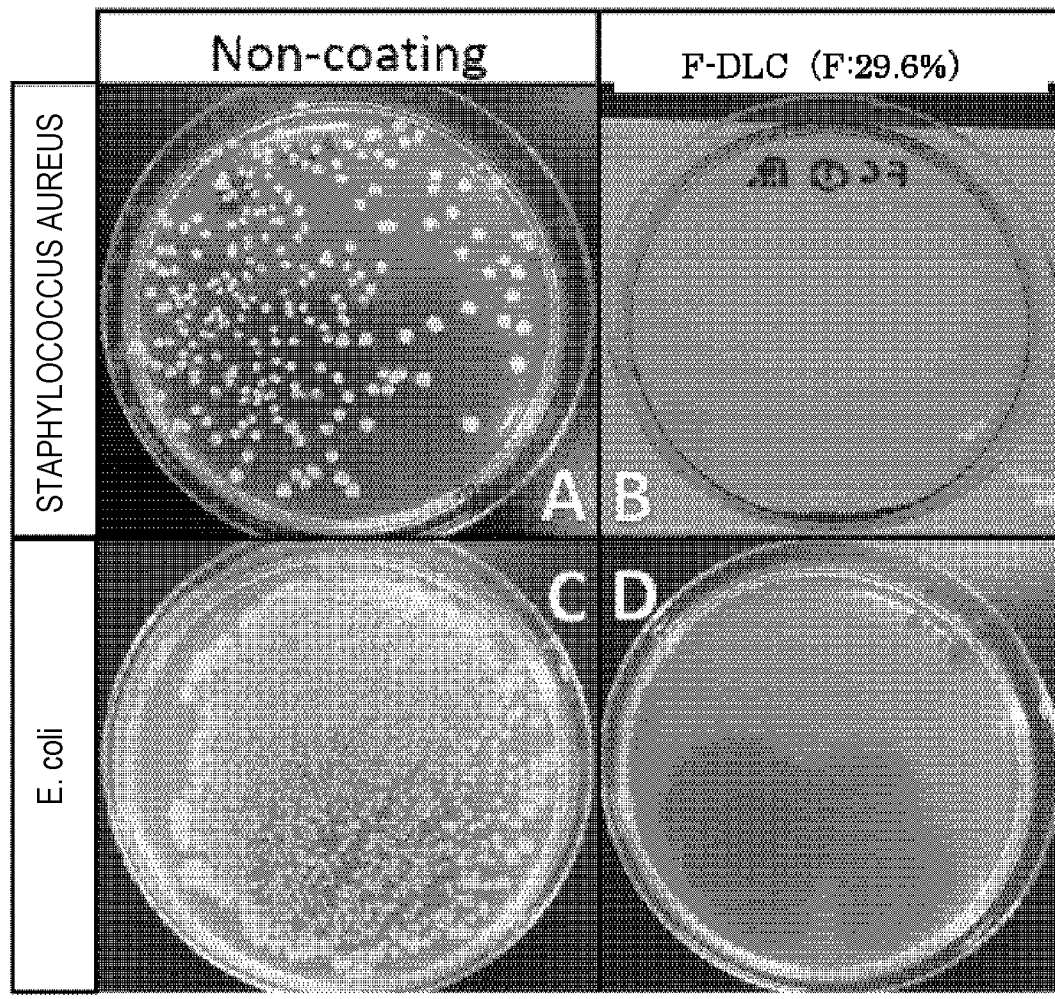
FIG. 2 illustrates pictures of culture results after culture for 24 hours.
Figure 3:
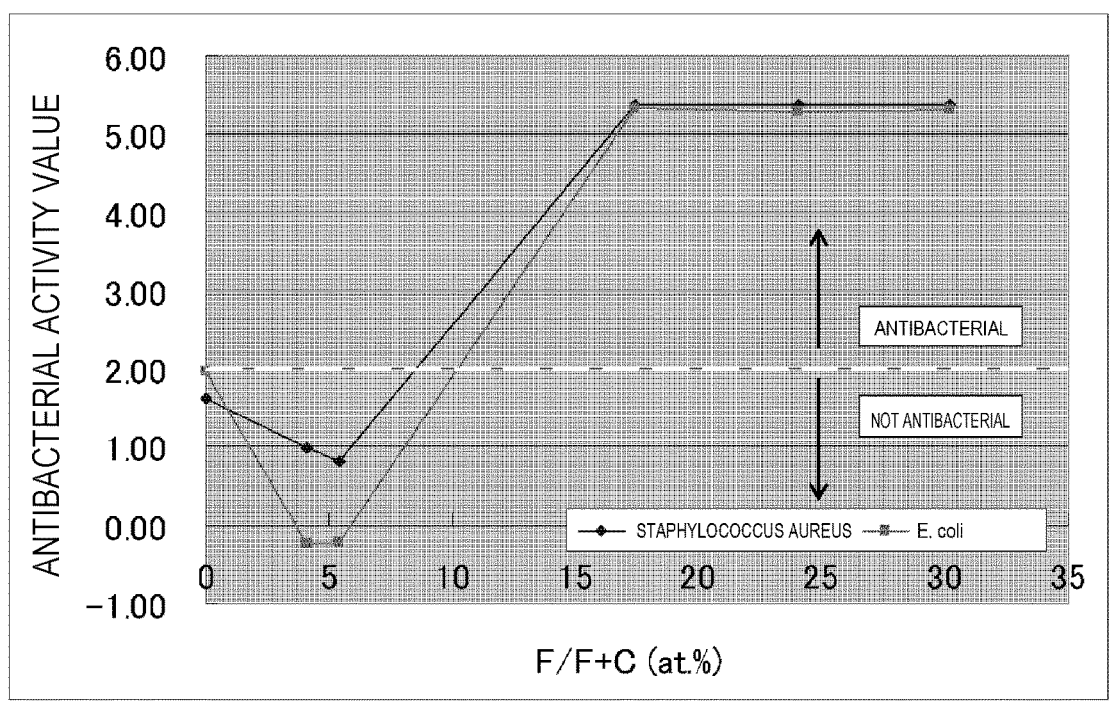
FIG. 3 illustrates a graph of a relation between fluorine concentration dependency and an antibacterial activity value of each film.

FIG. 2 illustrates culture results for checking the number of bacterial cells after the culture for 24 hours, FIG. 3 illustrates a graph of the relation between the fluorine concentration dependency and the antibacterial activity value of each film, and FIG. 4 illustrates a table listing the antibacterial activity value and the like of each film.

In an untreated sample, the number of viable cells of *E. coli* increased from $2.5 \times 10^4$ CFU to $4.0 \times 10^6$ CFU through the culture in 24 hours (C of FIG. 2). However, with an F-DLC film having an element ratio (F/(F+C)) of 30%, no bacteria were detected after the culture although bacteria existed in inoculum solution (equal to or smaller than 20 CFU; D of FIG. 2).

The same result was obtained for *Staphylococcus aureus*: the number of bacterial cells clearly increased for an untreated sample, but no bacteria were detected for an F-DLC film coated sample (B of FIG. 2).

As illustrated in FIGS. 3 and 4, the antibacterial activity value of the F-DLC film was 5.38 for *Staphylococcus aureus* and 5.33 for *E. coli*, and extremely high antibacterial activity with substantial sterilization was observed.

However, no significant antibacterial property was observed when the element ratio (F/(F+C)) was smaller than 17%, which indicates that a sufficient fluorine concentration is needed to obtain the antibacterial property.

[Nanoindentation Hardness]

Since a bone supported to, fixed to, replaced with, or inserted into an antibacterial member such as an implant moves in accordance with motion of the person, the bone generates friction and wear at an interface with the antibacterial member. Once a surficial film wears, inflammation due to wear powder and development of infection due to loss of the film potentially occur. In addition, a sufficient wear resistance is needed to assure the antibacterial property of the F-DLC film.

However, such a high wear resistance required for, for example, a DLC film formed on the surface of a working machine tool is unnecessary when it is assumed that the antibacterial member is used while being entirely or partially inserted into the body. In other words, the antibacterial member only needs to have a wear resistance sufficient for contact with a bone in the body or the like.

The nanoindentation hardness was measured by using an ultra-microhardness tester (nanoindenter) ENT-1100 manufactured by ELIONIX INC. with a pressing load of 1 mN by using a triangular pyramid Berkovich indenter.

A load with which a pressing depth into the F-DLC film was 1/10 of the film thickness approximately was selected, and the 10-point average thereof was obtained as the nanoindentation hardness.

The DLC film and each F-DLC film having a different element ratio (F/(F+C)) were formed on the surface of a test piece (having a diameter φ of 25 mm and a thickness of 3 mm) made of Ti alloy (TiAl6V4) so that the total film thickness thereof including an intermediate layer was 800 nm approximately.

As Comparative Examples, polytetrafluoroethylene [poly(1,1,2,2-tetrafluoroethylene): PTFE], which is known to have an antibacterial effect, and ultra high molecular weight polyethylene (UHMWPE), which is a biomaterial used for the head of an artificial joint as a slide part were used.

The PTFE was used to produce a square member having a size of 20 mm×20 mm and a thickness of 5 mm, and the nanoindentation hardness of the surface thereof was measured.

Figure 6:
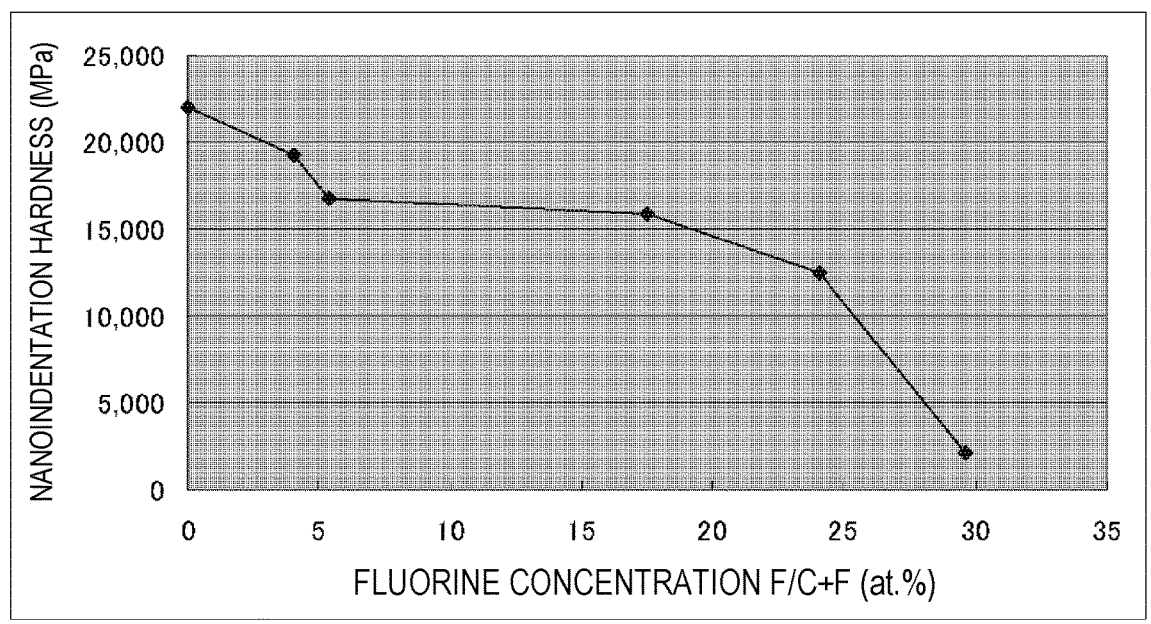
FIG. 6 illustrates a graph of a relation between an element ratio (F/(F+C)) and the nanoindentation hardness of each film.

FIG. 5 illustrates physical property evaluation results of the nanoindentation hardness and the like, and FIG. 6 illustrates a graph of the relation between the element ratio (F/(F+C)) and the nanoindentation hardness of the DLC film or each F-DLC film.

It is observed that the hardness decreases as the fluorine concentration of the F-DLC film increases.

[Friction and Wear Test]

A friction and wear test of each F-DLC film was performed.

The test was performed by a pin-on-disk method, and FPR-2100 manufactured by RESCHA CO., LTD. was used as a test machine. A femur (cortical bone) of a pig was processed to have a diameter φ of 2 mm and a length of 25 mm and used as a pin. Test conditions were as follows: the slide radius was 7 mm, the contact surface pressure was 1.5 MPa or higher, the slide speed was 20 mm/sec, and the slide distance was 80.6 m. To reproduce environment in a living body, the test was performed under wet environment by using pseudo joint fluid (normal saline solution containing 0.4 mg/ml of sodium hyaluronate) adjusted to the temperature of 37±2° C.

To evaluate a wear amount, the weight of each test piece was measured by an electronic balance in advance before the test and also measured again after the test, and the difference between the measurements was obtained as the wear amount.

Figure 7:
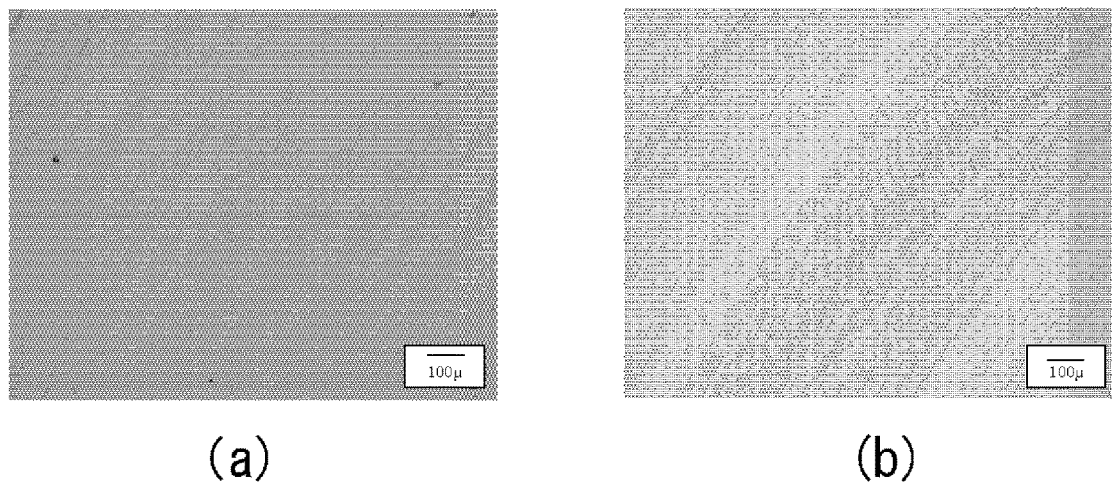
FIG. 7 illustrates, in (a) and (b), an optical microscope image of wear indentation of each film.
Figure 8:
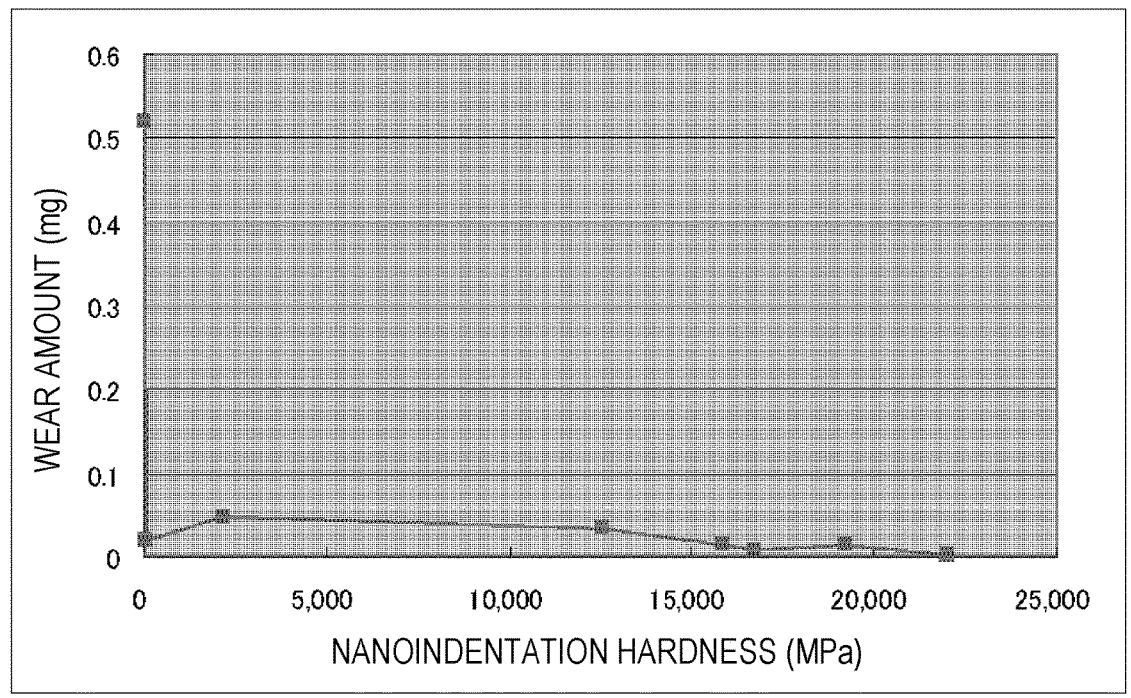
FIG. 8 illustrates a graph of a relation between the nanoindentation hardness and a wear amount of each film.

FIG. 7 illustrates, in (a) and (b), optical microscope images of wear indentation of the films. FIG. 8 illustrates a diagram of correlation between the wear amount and the hardness of each film.

The wear amount is extremely small for the DLC film and all F-DLC films as compared to PTFE, which indicates that F-DLC has excellent wear resistance under the pseudo living body environment although the hardness is low.

This is thought to be because a bone as a counterpart of friction has a Vickers hardness of up to 130 Hv approximately, which is up to 1,600 MPa in the nanoindentation hardness approximately, and is softer than F-DLC and thus F-DLC has a high wear resistance, whereas PTFE is softer than the bone and thus has an extremely decreased wear resistance.

Accordingly, the present invention is extremely soft for typical hard coating and thus cannot achieve a sufficient wear resistance, but the present invention is suitably applicable to body indwelling instruments for surgeries of bone and inter-bone support, fixation, replacement, and bone insertion, which are not slide parts, because a sufficient wear resistance can be achieved.

The larger film thickness provides a more excellent wear resistance, and thus the film thickness is preferably 500 nm or larger as in the present invention. However, the film thickness exceeding 10 μm leads to a longer time for deposition and is not preferable in terms of cost.

[Film Sticking Force Evaluation]

A Rockwell indentation test was performed to evaluate the sticking force of the F-DLC film when the base material plastically deforms. The test is a method of pressing an indenter against the film to largely plastically deform the base material and evaluating the existence of peeling of the film at a part around an indentation generated by the indenter, and widely known as a sticking force evaluation method in hard coating.

First, the DLC film and each F-DLC film having a different element ratio (F/(F+C)) were formed on the surface of a test piece made of SUS316. Then, a diamond indenter having a leading end angle of 120° was pressed against each film under a load of 150 kgf (C scale: HRC) to largely plastically deform the base material and measure the existence of film peeling generated around an indentation.

The evaluation was performed at six levels ranging from HR1 in which peeling is observed entirely around the indentation to HR6 in which no peeling is generated (FIG. 5). Typically, a close contact defect is determined at the level HR5 or lower.

Figure 9:
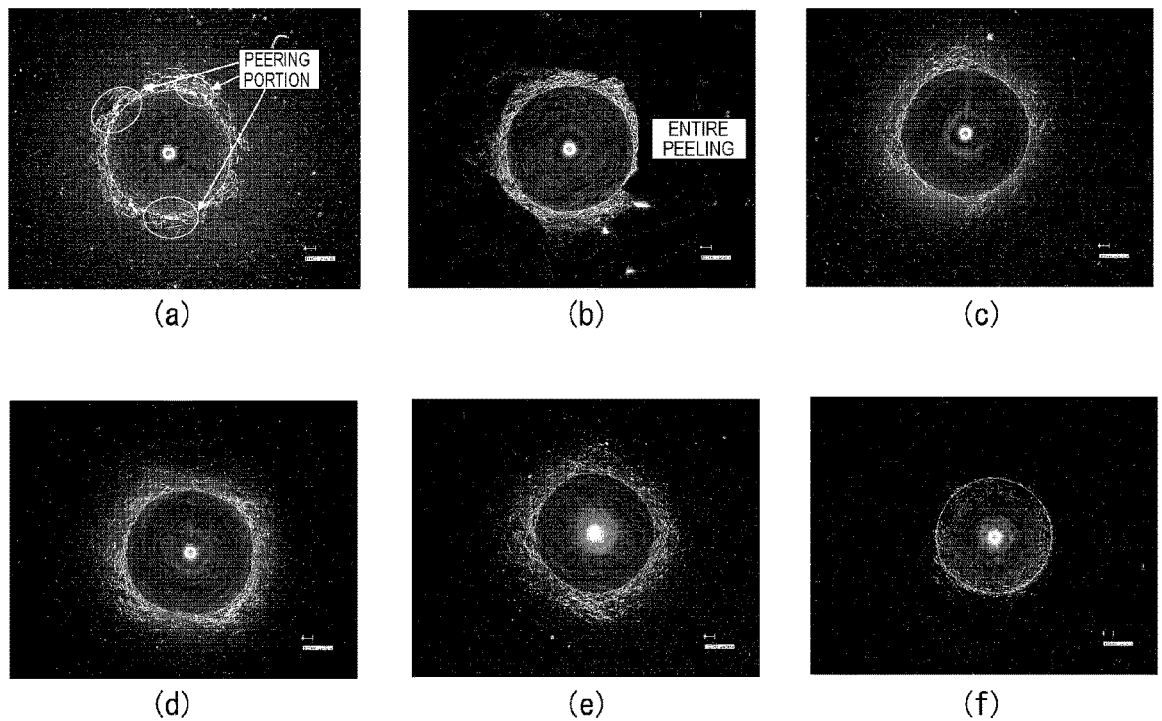
FIG. 9 illustrates a CCD image of HRC indentation of each film at a magnification of 100 times: a DLC film image in (a), an F-DLC film (4%) image in (b), an F-DLC (5%) image in (c), an F-DLC (17%) image in (d), an F-DLC (24%) image in (e), and an F-DLC (30%) image in (f).
Figure 10:
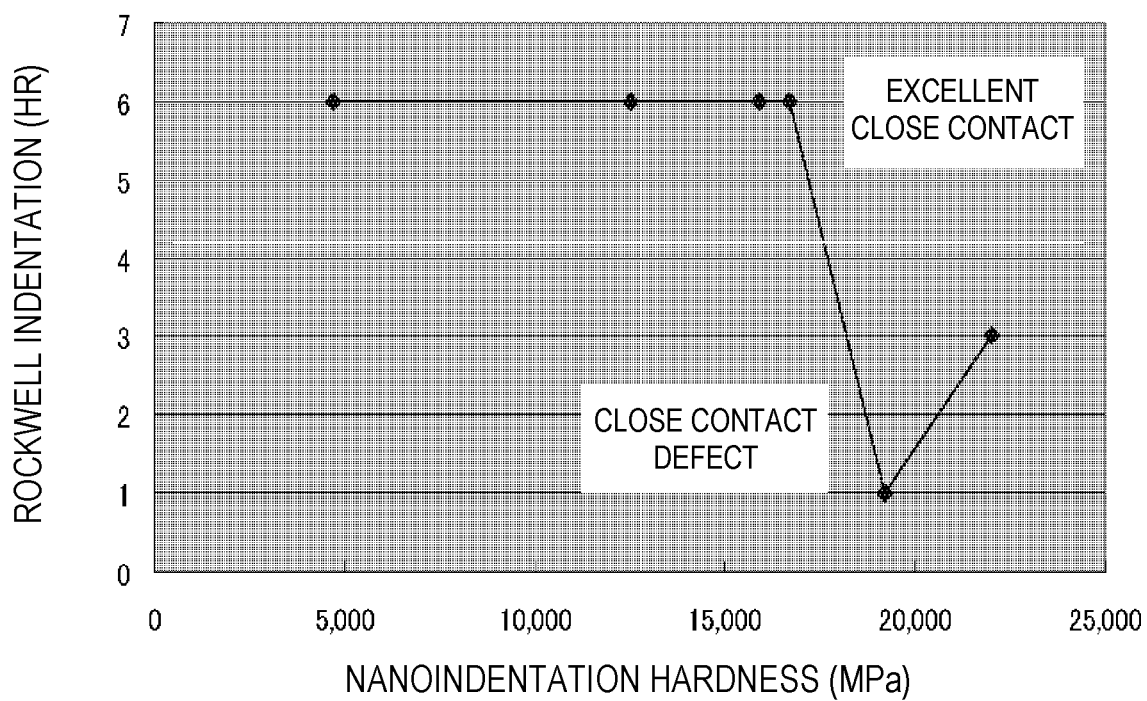
FIG. 10 illustrates a graph of the relation between the nanoindentation hardness and Rockwell indentation (peeling status).

FIG. 9 illustrates, in (a) to (f), CCD images of HRC indentations of the films at a magnification of 100 times. FIG. 10 illustrates a graph of the relation between the nanoindentation hardness and a Rockwell indentation (peeling status).

Ti alloy and SUS316, which are used for medical instruments, have low hardness, and thus when these materials are used as the base material, high stress is generated on the surface of the base material due to the hardness difference between the base material and each film when the base material is largely deformed. It is known that peeling is likely to occur to a film having high hardness for this reason, and the peeling problem is significant in the DLC film and each F-DLC film having particularly high hardness also due to high internal stress thereof.

The results of the test indicate that sufficient film sticking force and following property can be obtained even for the base material made of a soft material when the F-DLC film has a nanoindentation hardness of 16,000 MPa or smaller. When the nanoindentation hardness of the film is 10,000 MPa or smaller, the internal stress further decreases, and thus the following property of the film is maintained with an increased film thickness, which is more preferable.

[Electric Resistance]

The surface of a jig entirely or partially indwelled in the body is preferably electrically insulated to prevent corrosion of metal of the base material due to contact potential. In addition, the surface of a jig indwelled in the body for a long duration is desirably electrically insulated to prevent metal allergy.

Measurement by a two-terminal method using a tester with an inter-terminal distance of 10 mm found that each film had a high surface tolerance value of 40 MΩ or higher as illustrated with the table in FIG. 5 and thus had no problem with indwelling in the body.

Although the two-terminal method is simple, the film tolerance is sufficiently high when the base material is made of metal, and thus a value twice as large as electric resistance in a direction (direction of the film thickness) orthogonal to the plane of the film is measured in effect. With a sufficiently clean surface, the electric resistance does not depend on the measurement inter-terminal distance in effect, and the evaluation can be sufficiently performed through electric resistance measurement by a simple commercially available tester.

[Biological Safety]

A cytotoxicity test of each F-DLC film (the element ratio (F/(F+C))=30%) in the present invention was performed according to (ISO) 10993-5 Added note B as an international standard that defines a test for determining biological safety of a medical instrument.

A Chinese hamster V79 cells were used. Samples were circular disks made of titanium alloy (TiAl6V4) and having a diameter ϕ of 65 mm and a thickness of 5 mm. The samples include four untreated samples, four DLC-treated samples, and four F-DLC coated samples (the element ratio (F/(F+C))=30%).

Each sample was subjected to predetermined sterilization, added with 10 ml of an M05 culture medium for each surface area of 60 $cm^2$, and subjected to extraction in a 5% $CO_2$ incubator at 37° C. for 24 hours.

The Chinese hamster V79 cells were cultured with this extracted culture solution for seven days and then fixed with 10% neutral buffered formalin solution. Thereafter, colonies were dyed with added Giemsa stain solution, and the number of colonies and a colony formation rate were calculated (FIG. 11).

When non-extracted culture solution is control solution, it is typically determined that no cytotoxicity is present when colony formation performance is 70% or higher, or cytotoxicity is present when the colony formation performance is 30% or lower.

Figure 12:
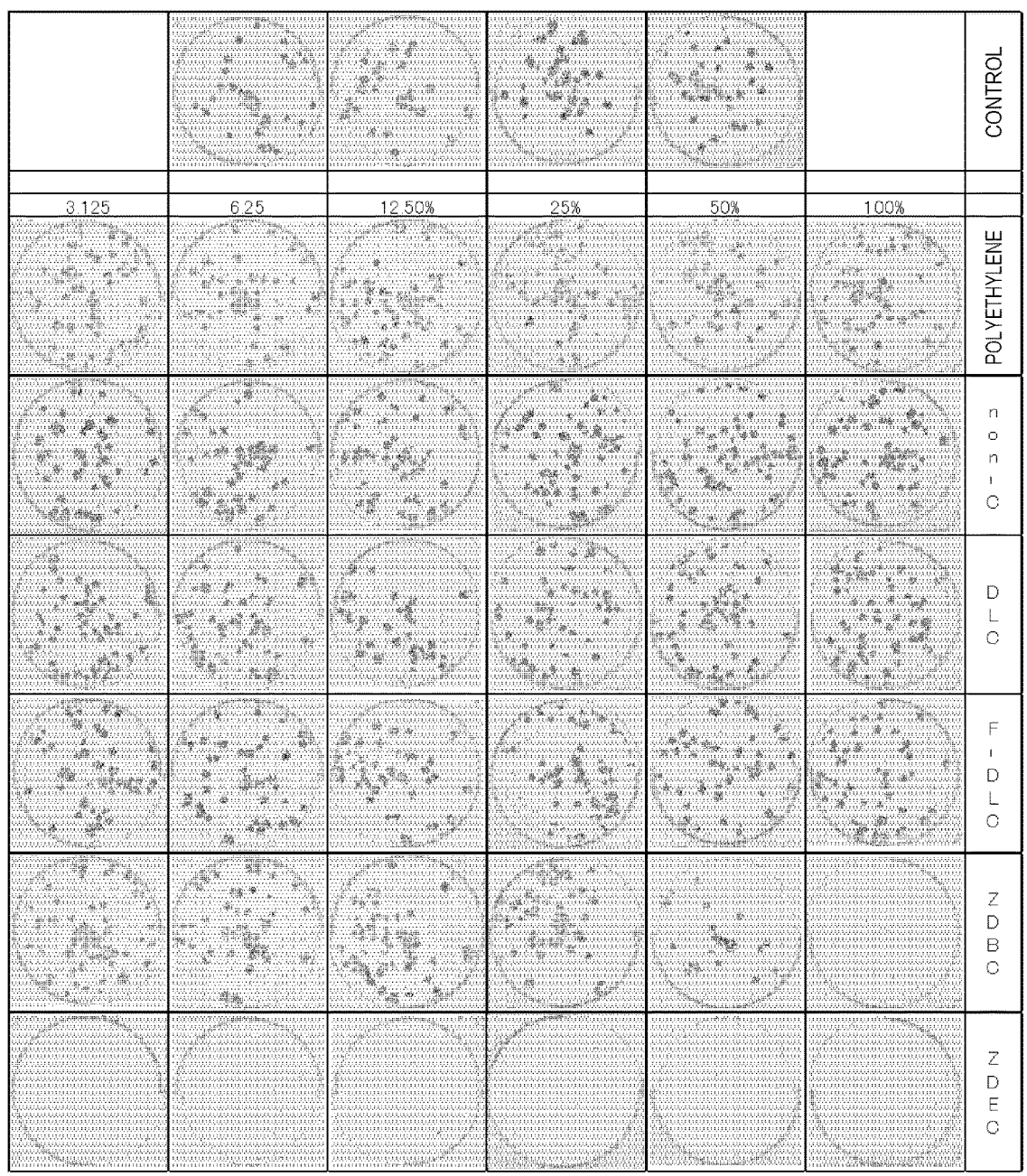
FIG. 12 illustrates a picture of a V79 cell colony formation state of each culture solution.

The colony formation rate of extracted solution was 105.8% for F-DLC, which indicates that no cytotoxicity was observed (FIG. 12).

Similarly, the colony formation rate of extracted solution was 100% or higher for DLC and unprocessed Ti alloy (FIGS. 11 and 12), which indicates that no cytotoxicity was observed.

Figure 13:
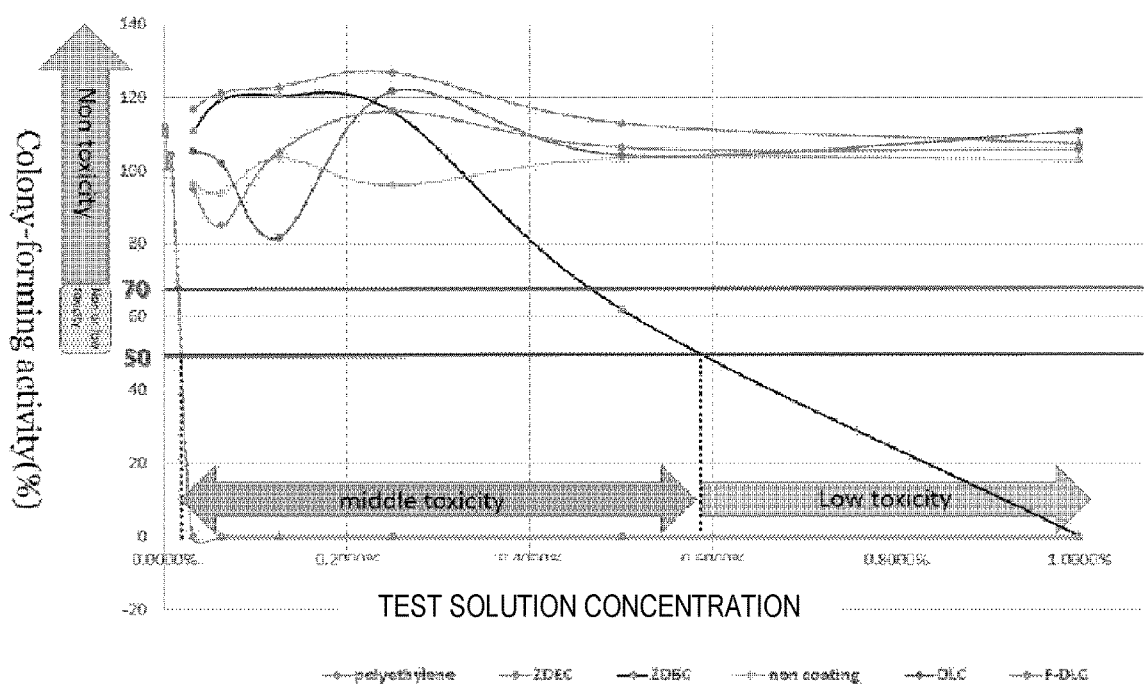
FIG. 13 illustrates a graph of the average value of the colony formation rate in comparison between a non-toxic target group (polyethylene) and a toxic target group (0.1% ZDEC, 0.25% ZDBC).

In comparison with a non-toxic target group (polyethylene) and a toxic target group (0.1% ZDEC, 0.25% ZDBC) that were tested simultaneously under the same condition as defined by ISO 10993-5 (FIG. 13), the colony formation rate of extracted solution for unprocessed Ti alloy, DLC, and F-DLC was substantially equal to that for non-toxic polyethylene, which indicates that no significant toxicity was observed.

Thus, F-DLC (the element ratio (F/(F+C))=30%) as the present invention has a high antibacterial property but has no living-body toxicity, and is suitable for coating for a medical instrument, and particularly preferable for a medical jig indwelled in the body.

[Osteoconductive Property]

The following describes experiment data related to influence of the antibacterial member according to the present invention on bone formation in vivo.

Samples were cylindrical and made of TiAl6V4 (slits each having a diameter of 5 mm, a length of 20 mm, a width of 1 mm, and a depth of 1 mm were formed at an interval of 1 mm). The samples include an F-DLC coated group (F-DLC group) and untreated samples (non-F-DLC group). The samples were inserted from outward to inward at three sites (shaft center, a close site from the center by 2 cm, and a far site from the center by 2 cm) of the right and left femurs of each of 12 female beagles aged 10 months.

To analyze bone kinetics, tetracycline was subcutaneously administered six days before and two days before the sample insertion, and calcein was subcutaneously administered six days before and two days before bone sample collection.

Bone samples were collected at elapse of four weeks, eight weeks, and 12 weeks, and immediately subjected to 70% ETOH fixation. In sample production, a cross-sectional polished bone sample of each femur was produced with non-decalcified Villanueva bone dye and subjected to bone morphogenic measurement (bone volume, the number of osteoblast cells, the number of osteoclast cells, bone calcification rate, bone formation rate, and osteoid width), and comparison was made between the F-DLC group and the non-F-DLC group (n=12).

<Results>

As illustrated with a table in FIG. 14, the bone volume in the sample slit increased in the F-DLC group as compared to the non-F-DLC group at elapse of 8 and 12 weeks. (8 weeks (57.53±8.70 $mm^2$ vs 35.37±5.09 $mm^2$ with $p<0.05$), and 12 weeks (72.71±5.13 $mm^2$ vs 61.17±5.88 $mm^2$ with $p<0.05$))

At elapse of 12 weeks, the number of osteoclast cells decreased in the F-DLC group as compared to the non-F-DLC group. (1.28±0.19 $mm^2$ vs 1.78±0.35 $mm^2$ with $p<0.05$). No significant difference was observed in the other bone formation parameters (the number of osteoblast cells, the bone calcification rate, the bone formation rate, and the osteoid width).

The F-DLC group had no difference from the non-F-DLC group in the number of osteoblast cells, the bone calcification rate, the bone formation rate, and the osteoid width, but in the F-DLC group, formation of a lamellar bone as a matured bone proceeded with significant decrease of the number of osteoclast cells and significant increase of the bone volume. This indicates that, in the F-DLC group, the bone volume increased and the remodeling phase was reached early due to shortening of the inflammatory phase of a bone adhesion process and reduction of bone absorption of osteoclast cells in bone remodeling.

When applied to an in-body instrument (instrumentation) for surgeries of bone and inter-bone support, fixation, replacement, and bone insertion, the F-DLC film of the present invention, which has an excellent osteoconductive property as described above, accelerates the bone adhesion process to fill the gap between the instrument and a bone with an early matured lamellar bone as compared to non-coated titanium alloy, thereby preventing loosening and sinking of the instrument from and to the bone and preventing complication in addition to infection, and thus is further preferable.

Conclusion

As described above, when the F-DLC film has an element ratio (F/(F+C)) of 17% to 72% and a nanoindentation hardness of 2,000 MPa to 16,000 MPa, a high wear resistance is obtained despite of a low film hardness and high close contact is maintained under the pseudo living body environment, and a high antibacterial property and a high osteoconductive property can be maintained for a long duration.

Example 2

[Mottled F-DLC Film]

The F-DLC film of the present invention maintains its functionalities even in a mottled pattern.

In the mottled pattern, the surface of the base material includes a region in which the F-DLC film exists and a region in which no F-DLC film exists in mixture. In the region in which no F-DLC film exists, the base material or the intermediate layer is exposed with no F-DLC layer, and thus no high antibacterial property is obtained.

Typically, no antibacterial effect is obtained at a part provided with no antibacterial treatment, and thus a sufficient antibacterial property is not obtained as a whole. However, according to the present invention, the F-DLC film has an extremely high antibacterial property and thus maintains a high antibacterial property as a whole in a mottled pattern. In addition, when the base material largely deforms, the film in a mottled pattern is likely to follow the deformation without peeling, thereby achieving higher durability.

In Example 2, the F-DLC film was formed on a test piece made of Ti alloy, and then the surface thereof was manually polished for 30 seconds by using a wrapping film (252X IMPERIAL RAPPING FILM ROLL manufactured by 3M Company, Grade: 1M1C, Type: F). Accordingly, a part at which the F-DLC film (third layer) was worn and torn in flaws was produced on the film.

Figure 15:
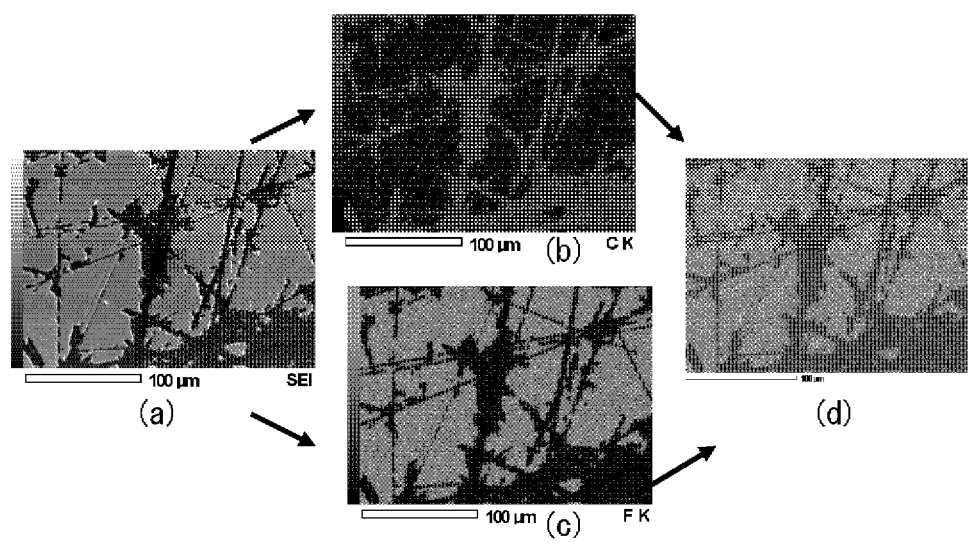
FIG. 15 illustrates a surficial image of distribution concentration of each element acquired through element analysis by energy dispersive X-ray spectroscopy using an electron microscope: an SEM image in (a), a carbon distribution image in (b), a fluorine distribution image in (c), and a carbon and fluorine superimposed image in (d).

FIG. 15 illustrates, in each of (a) to (d), a surficial image of element distribution concentration acquired through element analysis by the EDS of the surface. It is clear that fluorine and carbon distributions are separated from each other and the F-DLC film is mottled. Each side of the region in which no F-DLC film exists has a length of up to 50 µm approximately, which is significantly larger than a typical bacteria size of up to 1 µm. The F-DLC film may be mottled not only by the above-described post polishing method but also by a method of forming the F-DLC film while being masked in a certain pattern in advance or a method of forming holes in the film by using shot peening or laser after deposition.

[Antibacterial Property]

The antibacterial property of the surface of the F-DLC film in a mottled pattern was evaluated by a method same as that in Example 1 described above.

Test solution using *Staphylococcus aureus* (ATCC29214) and *E. coli* (ATCC25922) was used. Samples were circular disks made of TiAl6V4 and having a diameter φ of 25 mm and a thickness of 3 mm. The samples include eight unprocessed test pieces (control samples), eight test pieces on the surface of each of which the F-DLC film was formed in a flat shape, and eight test pieces on the surface of each of which the F-DLC film was formed in a mottled pattern.

The test bacterial solution was dropped on each sample, and the sample was covered with a film and cultured in a petri dish at 35° C. for 24 hours. The test solution after the culture was washed out of the film and a test piece, and then the number of viable cells per unit area was determined for each specimen by measuring the number of bacterial cells in the solution by the agar flat plate culture method, thereby calculating the antibacterial activity value.

Figures 16, 17:
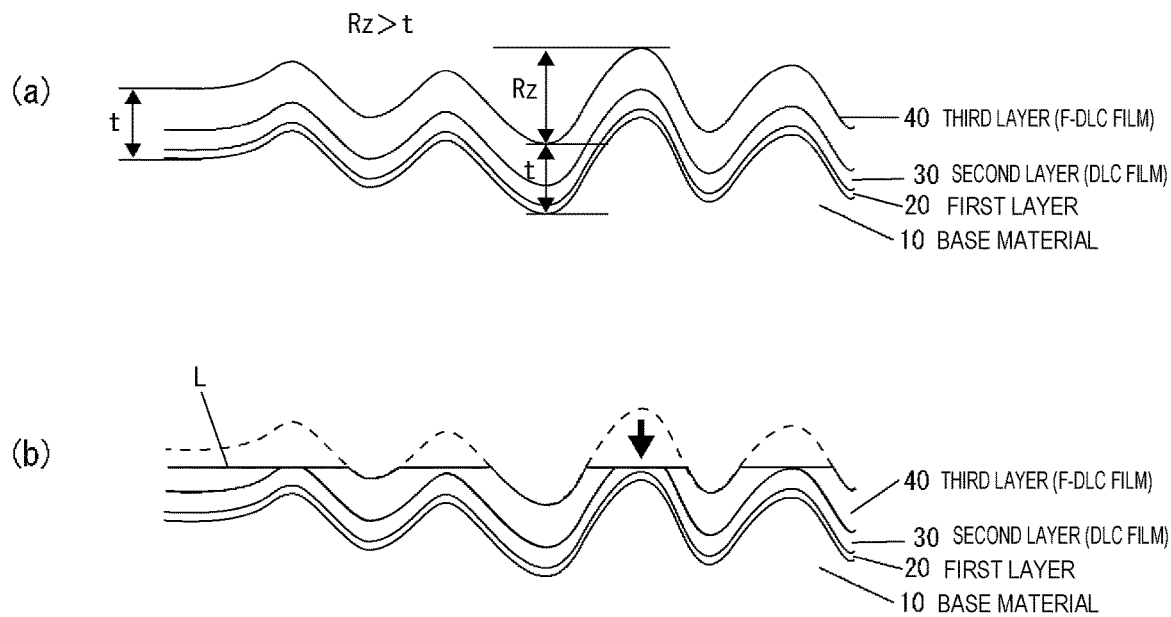
FIG. 16 illustrates a table illustrating the number of bacterial colonies after culture for 24 hours.
FIG. 17 is a cross-sectional view (a) schematically illustrating a state in which the first to third layers are formed on the base material under condition of Rz>z, and a diagram (b) after elapse of a certain duration.

FIG. 16 illustrates the number of bacterial colonies after the culture for 24 hours.

With the untreated samples, the number of viable cells of *Staphylococcus aureus* increased from $2.4 \times 10^4$ CFU to $1.4 \times 10^6$ CFU through the culture in 24 hours. However, with the F-DLC films in a flat shape and in a mottled pattern, no bacteria were detected after the culture in WPC treated samples and pseudo worn samples although bacteria existed in inoculum solution.

The same result was obtained for *Staphylococcus aureus*: the number of bacterial cells clearly increased for the untreated samples, but no bacteria were detected for the F-DLC films in a flat shape and a mottled pattern.

The antibacterial activity value of the F-DLC film in a mottled pattern was 5.0 for *Staphylococcus aureus* and 5.20 for *E. coli*, and extremely high antibacterial activity was observed.

[F-DLC Treatment on Irregular Surface]

The F-DLC film of the present invention maintains the antibacterial property when provided with irregularity treatment by shot peening or the like. Typically, the antibacterial member is formed in a smooth shape to prevent adhesion of bacteria, but F-DLC (the element ratio (F/(F+C))=17% or higher), which has an extremely high antibacterial property, maintains the antibacterial property even for an irregular surface.

In particular, it is found that the wear resistance and close contact can be maintained when the surface of the base material is an irregular surface and the F-DLC film is such a smooth surface that Rz>t holds, where t represents the thickness between the surface of the base material and the surface of the F-DLC film at deposition and Rz represents the maximum height of section for a surface roughness of the F-DLC film at deposition, and a high antibacterial property can be maintained even when the F-DLC film is partially peeled in a surgery operation or the like or worn at a slide surface of an artificial joint or the like.

FIG. 17 (a) illustrates a state at deposition of the F-DLC film in which Rz>t holds. FIG. 17 (b) illustrates a state after elapse of a certain time.

The F-DLC film, which is softer than the DLC film, becomes worn as time elapses after the deposition, and the surface thereof finally assumes a shape as illustrated with Line L. A highest place on the irregular surface of the F-DLC film at deposition, in other words, a place at which the sectional height of the surface roughness is maximum is a place that becomes thinnest due to wearing.

When the deposition is performed so that Rz>t holds, the F-DLC film is completely eliminated at the place at which the sectional height is maximum due to wearing and the DLC film is exposed as illustrated in FIG. 17 (b) after elapse of a certain duration. However, the wearing hardly proceeds thereafter since the DLC film has a high hardness. In this state, the F-DLC film sufficiently remains at a recessed place, and thus the antibacterial effect of the F-DLC film is maintained.

Figure 18:
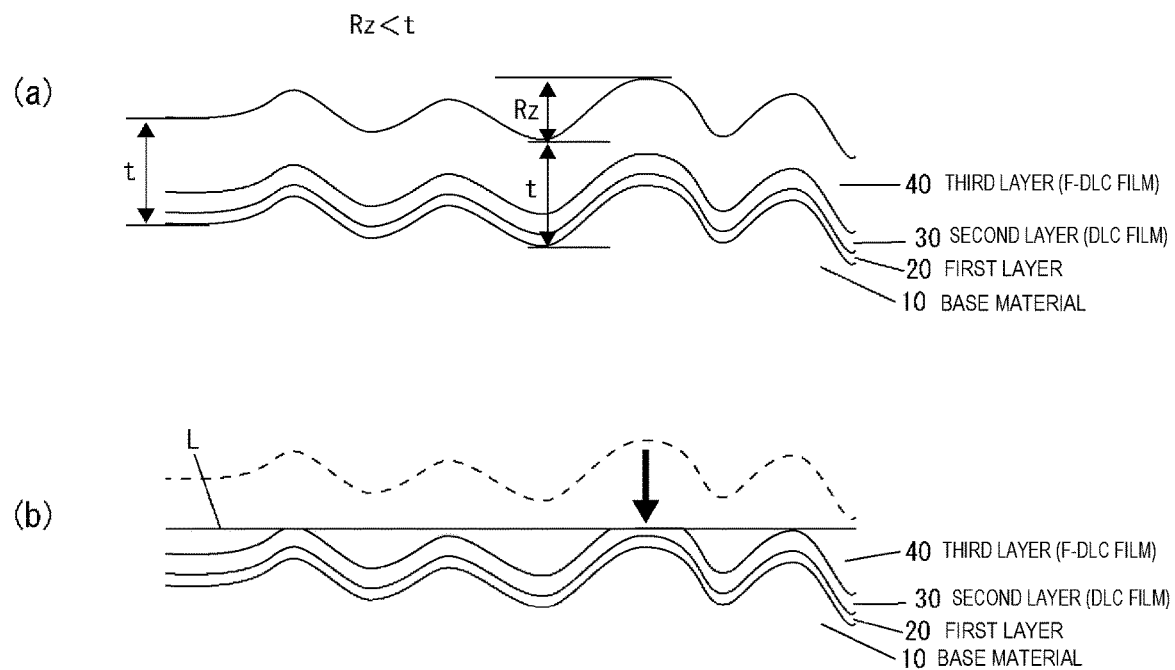
FIG. 18 is a cross-sectional view (a) schematically illustrating a state in which the first to third layers are formed on the base material under condition of Rz<z as a comparative example, and a diagram (b) after elapse of a certain duration.

When Rz<t holds at the deposition as illustrated in FIG. 18 (a), the F-DLC film is completely eliminated at the place at which the sectional height is maximum due to wearing and the DLC film is exposed as illustrated in FIG. 18 (b) after elapse of a certain duration. In this state, the remaining amount of the F-DLC film is small, and thus it is difficult to maintain the antibacterial effect of the F-DLC film.

[Irregularity Treatment of Base Material]

The surface of the base material was provided with shot peening treatment using fine particles and thereafter polished to remove minute fluff due to shot peening, and then the F-DLC film and the like were deposited on the surface.

The hardness of the surface of the base material is improved by the shot peening, and the base material is prevented from deforming when stress is applied from the outside, thereby improving the wear resistance. In addition, the hardness of the film and the base material surface is improved by decrease of the hardness difference between the DLC film and the F-DLC film, and thus stress applied on the interface therebetween is reduced when the base material deforms due to stress from the outside, thereby improving effective film sticking force.

Treatment conditions in the present example are as follows: pneumablaster P-SGF-3(A)S manufactured by Fuji Manufacturing Co., Ltd. was used to provide peening treatment on each place of the surface of a treatment target object by using steel #400 fine particles as shot material for 20 seconds at the pressure of 0.2 MPa (weak WPC condition) and 0.6 MPa (strong WPC condition). Thereafter, AERO LAP device YT-300 manufactured by Yamashita works Co., Ltd. was used to polish each place at a conveyer speed of 10/100 for 20 seconds by using standard media. Thereafter, cleaning was performed to remove residual media, and then an F-DLC film was deposited.

The irregularity treatment of the base material in the present invention is not limited to the shot peening treatment, but the same antibacterial effect for a long duration can be obtained by a publicly known surface treatment method when there are no sharp protrusions in a surface state with minute irregularities produced by using laser processing, filing, and a laser processed mold or a surface state provided with emboss processing or the like to have protrusions or recesses only. The coated base material is not limited to metal.

[Roughness Measurement]

FIG. 19 illustrates a table listing results of measurement of the surface roughness of each film.

In roughness measurement, an arithmetic average roughness Ra, a maximum height Rz, an outline curve element average length RSm, and a surface roughness maximum sectional height Rt were evaluated under conditions compliant with JIS B0651-2001 and JIS B0601-2001. A stylus surface roughness meter (SURFCOM FLEX manufactured by TOKYO SEIMITSU CO., LTD.) compliant with the JIS standard and using a conical stylus leading end shape having a leading end curvature radius of 2 μm and a leading end angle of 60° was used.

Measurement of each specimen was performed after calibration using a standard specimen. Measurement conditions were as follows: a cutoff value λc was 0.8 mm, a reference length lr was 0.8 mm, and a measurement length ln was 4 mm.

As comparative examples, a segment F-DLC film and a DLC+WPC+F-DLC specimen were produced. The surface of the segment F-DLC film was covered with a metal mesh at deposition of F-DLC to leave an undeposited part in a lattice shape. The DLC+WPC+F-DLC specimen was obtained by covering the surface of a base material made of Ti alloy with a normal no-fluorine containing DLC film in advance, performing shot peening treatment on the surface, and thereafter covering the surface with an F-DLC film.

[Friction and Wear Test]

A friction and wear test of an F-DLC film deposited to have an irregular surface was performed by a method same as that in [friction and wear test] in Example 1.

The test was performed by a pin-on-disk method, and FPR-2100 manufactured by RESCHA CO., LTD. was used as a test machine. A femur (cortical bone) of a pig was processed to have a diameter φ of 2 mm and a length of 25 mm and used as a pin.

A test piece was produced by performing surface treatment on Ti alloy (TiAl6V4; having a diameter φ of 25 mm and a thickness of 3 mm) under various conditions.

Test conditions were as follows: the slide radius was 7 mm, the contact surface pressure was 1.5 MPa or higher, the slide speed was 20 mm/sec, and the slide distance was 72 m. To reproduce environment in a living body, the test was performed under wet environment by using pseudo joint fluid (normal saline solution containing 0.4 mg/ml of sodium hyaluronate) adjusted to the temperature of 37±2° C.

FIG. 20 illustrates an optical microscope image of wear indentation of each specimen after the test.

The segment F-DLC has a too small irregularity height (≅Rz) approximately equal to the film thickness, and thus does not have a sufficient wear resistance. The DLC+WPC+F-DLC has a sufficient Rz value but has minute protrusions in a small irregularity period with a small RSm value and a large Ra value, and thus the wear resistance thereof is degraded.

However, appropriate recesses are formed in the week WPC+F-DLC and the strong WPC+F-DLC, and thus excellent wear resistance is obtained. In addition, wearing proceeds in a mottled pattern similarly to pseudo wear treatment, and thus a high antibacterial property is sufficiently maintained when wearing proceeds.

Thus, a minute and smooth irregular surface for which the surface roughness element average length RSm is 40 μm to 200 μm and Ra is 0.1 μm to 1 μm is particularly preferable.

[Antibacterial Property]

The antibacterial property of the surface of the F-DLC film in a mottled pattern was evaluated by a method same as that in Example 1 described above.

Test solution using *Staphylococcus aureus* (ATCC29214) and *E. coli* (ATCC25922) was used. Samples were circular disks made of TiAl6V4 and having a diameter φ of 25 mm and a thickness of 3 mm. The samples include eight unprocessed test pieces (control samples), and eight test pieces, the surface of each of which was provided with the irregularity treatment and the F-DLC film deposition under various conditions.

The test bacterial solution was dropped on each sample, and the sample was covered with a film and cultured in a petri dish at 35° C. for 24 hours. The test solution after the culture was washed out of the film and a test piece, and then the number of viable cells per unit area was determined for each specimen by measuring the number of bacterial cells in the solution by the agar flat plate culture method, thereby calculating the antibacterial activity value.

FIG. 21 illustrates a table listing the antibacterial activity value after the culture for 24 hours.

With the untreated samples, the number of viable cells of *Staphylococcus aureus* increased from $2.4 \times 10^4$ CFU to $1.4 \times 10^6$ CFU through the culture in 24 hours. However, with the F-DLC films in a flat shape and a mottled pattern, no bacteria were detected after the culture even in WPC treated samples although bacteria existed in inoculum solution.

The same result was obtained for *Staphylococcus aureus*: the number of bacterial cells clearly increased for the untreated samples, but no bacteria were detected for the F-DLC films in a flat shape and in an irregular shape.

The antibacterial activity values of all irregular F-DLC films were 5.3 or 5.0 for *Staphylococcus aureus* and 5.31 or 5.20 for *E. coli*, and extremely high antibacterial activity was observed.

[Bone Adhesion Improvement Due to Irregular Surface]

The application to body indwelling instruments (instrumentation) for surgeries of bone and inter-bone support, fixation, replacement, and bone insertion is further preferable when the surface is provided with the irregularity treatment. This is because bone adhesion improvement and osteoconductive improvement by an anchor effect or the like due to the surface irregularities are expected.

Conclusion

As described above, the antibacterial effect of an F-DLC film can be maintained even when the F-DLC film is disposed in a mottled pattern.

INDUSTRIAL APPLICABILITY

The present invention is an antibacterial member that maintains a high antibacterial property and a high osteoconductive property for a long duration, and has industrial applicability.

REFERENCE SIGNS LIST 10 base material
20 carbon compound layer
30 DLC film
40 F-DLC film

The invention claimed is:

1. An antibacterial member comprising a base material having an irregular surface, wherein
   at least a DLC film containing no fluorine and a DLC film (F-DLC film) containing fluorine are sequentially coated on the surface of the base material,
   the F-DLC film is provided at least partially or entirely on an outermost surface of the base material,
   the F-DLC film has an element ratio (F/(F+C)) of 17% to 72% and a nanoindentation hardness of 2,000 MPa to 16,000 MPa, and
   Rz>t holds, where t represents a thickness between the surface of the base material and a surface of the F-DLC film at deposition and Rz represents a maximum height of section for a surface roughness of the F-DLC film at deposition.

2. The antibacterial member according to claim 1, wherein the antibacterial member is a medical instrument inserted into or fixed to a bone.

3. An antibacterial member comprising a DLC film (F-DLC film) containing fluorine at least partially or entirely on an outermost surface of a base material, wherein
   the F-DLC film has an element ratio (F/(F+C)) of 17% to 72% and a nanoindentation hardness of 2,000 MPa to 16,000 MPa, and
   a non-hydrogen DLC film is formed as a first layer directly above the base material, then a hydrogen-containing DLC film containing no fluorine is formed as a second layer, and then the F-DLC film is formed as a third layer.

4. The antibacterial member according to claim 3, wherein the F-DLC film is disposed in a mottled pattern.

5. The antibacterial member according to claim 3, wherein
   at least a DLC film containing no fluorine and the F-DLC film are sequentially coated on a surface of the base material,
   the surface of the base material is an irregular surface, and
   Rz>t holds, where t represents a thickness between the surface of the base material and a surface of the F-DLC film at deposition and Rz represents a maximum height of section for a surface roughness of the F-DLC film at deposition.

6. The antibacterial member according to claim 3 wherein the antibacterial member is a medical instrument inserted into or fixed to a bone.

7. The antibacterial member according to claim 4 wherein the antibacterial member is a medical instrument inserted into or fixed to a bone.

8. The antibacterial member according to claim 5 wherein the antibacterial member is a medical instrument inserted into or fixed to a bone.

* * * * *